(12) United States Patent  (10) Patent No.: US 8,333,936 B2
Miyashita et al. (45) Date of Patent: Dec. 18, 2012

(54) REAGENT SPLITTING/DISPENSING METHOD BASED ON REAGENT DISPENSING NOZZLE AND REAGENT SPLITTING/DISPENSING MECHANISM

(75) Inventors: Noe Miyashita, Tokyo (JP); Hideyuki Noda, Tokyo (JP); Masahiro Okanojo, Tokyo (JP)

(73) Assignee: Hitachi Plant Technologies, Ltd., Tokyo (JP)

( * ) Notice: Subject to any disclaimer, the term of this patent is extended or adjusted under 35 U.S.C. 154(b) by 2 days.

(21) Appl. No.: 13/009,037

(22) Filed: Jan. 19, 2011

(65) Prior Publication Data

US 2011/0176975 A1 Jul. 21, 2011

(30) Foreign Application Priority Data

Jan. 19, 2010 (JP) ................................. 2010-009037

(51) Int. Cl.
*B01L 3/02* (2006.01)
*G01N 1/10* (2006.01)

(52) U.S. Cl. ........ 422/518; 422/501; 422/504; 422/505; 422/509; 436/180; 436/53; 436/54

(58) Field of Classification Search .................. 436/180, 436/807, 43, 53, 54, 174; 422/501, 504–505, 422/509, 516, 518, 519
See application file for complete search history.

(56) References Cited

U.S. PATENT DOCUMENTS

| 4,927,765 | A  |   | 5/1990  | Saxon et al. |
| 5,443,791 | A  |   | 8/1995  | Cathcart et al. |
| 5,525,302 | A  | * | 6/1996  | Astle .............................. 422/511 |
| 5,927,547 | A  | * | 7/1999  | Papen et al. ..................... 222/57 |
| 6,079,283 | A  | * | 6/2000  | Papen et al. ................. 73/864.11 |
| 6,220,075 | B1 | * | 4/2001  | Papen et al. ..................... 73/1.74 |
| 6,238,857 | B1 |   | 5/2001  | Hattori et al. |
| 6,521,187 | B1 | * | 2/2003  | Papen .......................... 422/504 |
| 6,551,557 | B1 | * | 4/2003  | Rose et al. ..................... 422/502 |
| 6,579,724 | B2 | * | 6/2003  | Woodward .................... 436/180 |
| 6,592,825 | B2 | * | 7/2003  | Pelc et al. ..................... 422/521 |
| 7,169,616 | B2 | * | 1/2007  | Johnson et al. ............... 436/180 |
| 7,247,487 | B2 | * | 7/2007  | Jacobs et al. ................... 436/53 |
| 7,413,710 | B2 | * | 8/2008  | Lisec et al. ................... 422/417 |
| 7,479,391 | B2 | * | 1/2009  | Bjornson et al. ............... 436/54 |
| 7,727,476 | B2 | * | 6/2010  | Ingenhoven et al. ......... 422/511 |
| 7,964,160 | B2 | * | 6/2011  | Zuppiger et al. .............. 422/500 |

(Continued)

FOREIGN PATENT DOCUMENTS

EP         0 289 789         11/1988

(Continued)

OTHER PUBLICATIONS

EP Search Report of Appln. 10197321.2 dated Dec. 2, 2011 in English.

(Continued)

*Primary Examiner* — Brian R Gordon
(74) *Attorney, Agent, or Firm* — Antonelli, Terry, Stout & Kraus, LLP.

(57) ABSTRACT

The present invention provides for a reagent splitting/dispensing device and method that can prevent contamination of an operation fluid when a reagent dispensing nozzle is in a waiting state and prevent falling of a droplet. The reagent splitting/dispensing method includes disposing and adjusting an air layer between an interface of an operation fluid and a reagent aspirated and subsequently dispensed from a nozzle tip end in an reagent dispensing nozzle.

7 Claims, 8 Drawing Sheets

U.S. PATENT DOCUMENTS

| | | | |
|---|---|---|---|
| 8,100,293 B2 * | 1/2012 | Mukaddam et al. | 222/1 |
| 2001/0014477 A1 * | 8/2001 | Pelc et al. | 436/49 |
| 2001/0016177 A1 * | 8/2001 | Pelc et al. | 422/100 |
| 2002/0064482 A1 * | 5/2002 | Tisone et al. | 422/100 |
| 2003/0049863 A1 * | 3/2003 | Woodward | 436/180 |
| 2004/0072365 A1 * | 4/2004 | Rose et al. | 436/180 |
| 2004/0231438 A1 * | 11/2004 | Schwartz | 73/864.17 |
| 2004/0259268 A1 * | 12/2004 | Jacobs et al. | 436/180 |
| 2006/0039824 A1 | 2/2006 | Onuma | |
| 2007/0155019 A1 * | 7/2007 | Johnson et al. | 436/180 |
| 2007/0202608 A1 * | 8/2007 | Uffenheimer et al. | 436/180 |
| 2008/0241871 A1 | 10/2008 | Okanojo et al. | |
| 2009/0142785 A1 | 6/2009 | Osato et al. | |
| 2009/0298129 A1 * | 12/2009 | Spence et al. | 435/91.2 |
| 2011/0111506 A1 * | 5/2011 | Zuppiger | 436/8 |

FOREIGN PATENT DOCUMENTS

| | | |
|---|---|---|
| EP | 0 411 620 | 2/1991 |
| JP | 52-043487 | 4/1977 |
| JP | 62-228952 | 10/1987 |
| JP | 11-155597 | 6/1999 |
| JP | 2008-249628 | 10/2008 |
| JP | 2009-139115 | 6/2009 |

OTHER PUBLICATIONS

Japanese Search Report of Appln. No. 2010-009037 dated Oct. 19, 2011.

Singapore Search report and Written Opinion of Appln. No. 201009257-5 dated Jun. 25, 2012 in English.

* cited by examiner

REAGENT SPLITTING/DISPENSING METHOD BASED ON REAGENT DISPENSING NOZZLE AND REAGENT SPLITTING/DISPENSING MECHANISM

BACKGROUND

1. Field of the Invention

The present invention relates to a mechanism that splits/dispenses a trace amount of a liquid (micro order), and more particularly, to a method that splits/dispenses a reagent by a reagent dispensing nozzle in a luminescence measuring device and a mechanism thereof.

2. Description of the Related Art

In various clinical medicine sites, food factories, medicinal drug manufacturing factories, and basic research sites, an aseptic work environment and predetermined biological cleanliness are required. In an environment where the biological cleanliness is required, the number of microorganisms (the number of viable bacteria) in the air (floating bacteria in the air), the number of falling bacteria, and the number of adhesive bacteria are measured. As a method that measures the number of floating bacteria in the air, it is general to use a sampler of the floating bacteria in the air to collect the floating bacteria by natural falling of the floating bacteria or sucking air of a constant amount in collecting the floating bacteria.

In this method, the floating bacteria are collected on an agar plate and are cultured by an incubator for two or three days, and the number of colonies generated after culturing is used as the number of bacteria. However, in this method, a long-time is needed to culture the viable bacteria.

Meanwhile, as a method that enables measurement of the number of microorganisms in a short time, a method that measures adenosine triphosphate (ATP) corresponding to a component in a cell by a bioluminescence method and converts the number of microorganisms is known.

In the bioluminescence method, a luciferin-luciferase luminescence reaction is used, the ATP amount is calculated from the luminescence amount of light generated by mixing and reacting a luminescence reagent containing substrate luciferin and enzyme luciferase and a sample solution containing the ATP extracted from the cells of the microorganisms, and the number of viable bacteria is calculated on the basis of the ATP amount per viable bacterium. In Japanese Patent Application Laid-Open (JP-A) No. 11-155597, a kit that measures the number of viable bacteria using the luminescence reaction is disclosed.

According to the method that measures the number of viable bacteria using the kit disclosed in JP-A No. 11-155597, a measurement time can be decreased. However, when the viable bacteria of the minute amount are measured, the luminescence amount becomes the minute amount. For this reason, background luminescence is greatly affected by mixing of the remaining ATP or the ATP other than the measurement object, and superior measurement precision cannot be obtained.

Meanwhile, in JP-A No. 2008-249628, a luminescence measuring device that can suppress background luminescence due to viable bacteria adhered to a nozzle to dispense a reagent or a remaining ATP and can quickly measure luminescence with high precision is disclosed.

According to the luminescence measuring device that is disclosed in JP-A No. 2008-249628, even in luminescence measurement where the viable bacteria of the minute amount are measured, it is assumed that the viable bacteria of the minute amount can be quickly measured with high precision. However, when the viable bacteria of the minute amount are measured by the luminescence measuring device, a measurement value may be greatly affected by contamination in the device.

SUMMARY OF THE INVENTION

Accordingly, it is an object of the present invention to provide a splitting/dispensing method based on a reagent dispensing nozzle and a reagent splitting/dispensing mechanism that can prevent contamination of an operation fluid in the reagent dispensing nozzle to split/dispense a reagent when the reagent dispensing nozzle is in a waiting state or generation of cross contamination due to falling of a droplet when the reagent dispensing nozzle is moved, and split/dispense the reagent with high precision.

To solve the aforementioned problem to be solved by the invention, the reagent splitting/dispensing method based on a reagent dispensing nozzle that controls a split amount or a dispensation amount of a reagent by an operation fluid disposed in the reagent dispensing nozzle, the reagent splitting/dispensing method is featured by including the following: a waiting process of disposing a first air layer between an interface of the operation fluid and a nozzle tip end in the reagent dispensing nozzle; a first moving process of moving the reagent dispensing nozzle to the position right above the reagent becoming a split object; a second moving process of depositing the nozzle tip end in the reagent; a reagent splitting process of decreasing the occupation amount of the operation fluid in the reagent dispensing nozzle and filling the reagent into the reagent dispensing nozzle from the nozzle tip end; a third moving process of evacuating the tip end of the reagent dispensing nozzle from the reagent; a reagent protecting process of disposing a second air layer between an interface of the split reagent and the nozzle tip end; a fourth moving process of moving the reagent dispensing nozzle to the reagent dispensation position, after the reagent protecting process; a reagent dispensing process of increasing the occupation amount of the operation fluid in the reagent dispensing nozzle and ejecting the split reagent; an operation fluid protecting process of disposing the first air layer between the interface of the operation fluid and the nozzle tip end, after dispensing the reagent; and a fifth moving process of evacuating the reagent dispensing nozzle to the waiting position, in a state where the first air layer is disposed between the interface of the operation fluid and the nozzle tip end.

Also, the reagent splitting/dispensing method having the aforementioned characteristic features preferably includes the following steps: an air layer adjusting process of increasing the occupation amount of the operation fluid in the reagent dispensing nozzle and decreasing the occupation amount of the first air layer, between the first moving process and the second moving process. By using these processes, when the reagent is filled into the reagent dispensing nozzle, the capacity of the first air layer that is disposed between the reagent and the interface of the operation fluid can be decreased. Thereby, the splitting/dispensing error of the reagent due to the compression or expansion of the air layer can be decreased.

Also, the reagent splitting/dispensing method having the aforementioned characteristic may includes the following: a temporary evacuating process of moving the reagent dispensing nozzle to the operation fluid discharge position after the reagent dispensing process; and an operation fluid ejecting process of ejecting a part of the operation fluid from the nozzle tip end, at the operation fluid discharge position. By using these processes, the operation fluid that exists near the interface where the possibility of the reagent being mixed or contaminated is high can be discharged. Thereby, generation of the cross contamination of the reagent or the contamination of the reagent can be prevented.

Further, in the reagent splitting/dispensing method having the aforementioned characteristics, it is preferable that, in the reagent dispensing process, the process proceeds to the temporary evacuating process, after the first air layer remains. By adopting these units, the reagent that is filled into the reagent dispensing nozzle can be completely ejected, and the operation fluid in the reagent filled nozzle can be prevented from being ejected.

Also, in order to solve the aforementioned problems to be solved by the invention, the reagent splitting/dispensing mechanism according to an exemplary embodiment of the invention includes a triaxial actuator in which a movement axis in a horizontal direction is set to an X axis and a Y axis and a movement axis in a vertical direction is set to a Z axis, a reagent dispensing nozzle which is moved by the triaxial actuator, and a pump unit which is connected to the reagent dispensing nozzle an controls an operation fluid disposed in the reagent dispensing nozzle. The reagent splitting/dispensing mechanism is featured by including: a control unit which outputs a first air layer arrangement signal to decrease the occupation amount of the operation fluid in the nozzle and dispose a first air layer between an interface of the operation fluid and a nozzle tip end in the reagent dispensing nozzle to the pump unit, outputs a first movement signal to move the reagent dispensing nozzle to the position right above the reagent becoming a split object and a second movement signal to deposit the nozzle tip end in the reagent to the triaxial actuator after the first air layer is disposed in the reagent dispensing nozzle, outputs a reagent split signal to decrease the occupation amount of the operation fluid in the nozzle and fill the reagent into the reagent dispensing nozzle from the nozzle tip end to the pump unit after the nozzle tip end is deposited in the reagent, outputs a third movement signal evacuate the tip end of the reagent dispensing nozzle from the reagent to the triaxial actuator, outputs a reagent protection signal to dispose a second air layer between an interface of the split reagent and the nozzle tip end to the pump unit, outputs a fourth movement signal to move the reagent dispensing nozzle to the reagent dispensation position to the triaxial actuator, after the second air layer is disposed in the reagent dispensing nozzle, outputs a reagent dispensation signal to increase the occupation amount of the operation fluid in the reagent dispensing nozzle and eject the reagent to the pump unit, after the reagent dispensing nozzle reaches the reagent dispensation position, outputs an operation fluid protection signal to decrease the occupation amount of the operation fluid in the reagent dispensing nozzle and dispose the first air layer between the interface of the operation fluid and the nozzle tip end to the pump unit, after the reagent is ejected from the reagent dispensing nozzle, and outputs a fifth movement signal to evacuate the reagent dispensing nozzle where the first air layer is disposed after the reagent is dispensed to the waiting position to the triaxial actuator.

Also, in the reagent splitting/dispensing mechanism having the aforementioned characteristic features, the control unit outputs an air layer adjustment signal to increase the occupation amount of the operation fluid in the reagent dispensing nozzle to the pump unit, between the output of the first movement signal and the output of the second movement signal. By using the control unit having the above configuration, when the reagent is filled into the reagent dispensing nozzle, the capacity of the first air layer that is disposed between the reagent and the interface of the operation fluid can be decreased. Thereby, the splitting/dispensing error of the reagent due to the compression or expansion of the air layer can be decreased.

In the reagent splitting/dispensing mechanism having the aforementioned characteristic features, it is preferable that the control unit outputs a temporary evacuation signal to move the reagent dispensing nozzle to the operation fluid discharge position to the triaxial actuator, after the reagent dispensation signal is output, and the control unit outputs an operation fluid ejection signal to increase the occupation amount of the operation fluid in the reagent dispensing nozzle to eject a part of the operation fluid from the tip end of the reagent dispensing nozzle moved to the operation fluid discharge position, to the pump unit. By using the control unit having the above configuration, the operation fluid that exists near the interface where the possibility of the reagent being mixed or contaminated is high can be discharged. Thereby, generation of the cross contamination of the reagent in the reagent dispensing nozzle or the contamination of the reagent can be prevented.

In the reagent splitting/dispensing mechanism having the aforementioned characteristic features, the reagent dispensation signal is a signal to control the occupation amount of the operation fluid to completely eject the reagent filled into the reagent dispensing nozzle and eject a part of the first air layer. By adopting these units, the reagent that is filled into the reagent dispensing nozzle can be completely ejected, and the operation fluid in the reagent filled nozzle can be prevented from being ejected.

In the reagent splitting/dispensing mechanism that has the above characteristics, the pump unit is preferably configured as a syringe pump. By using this configuration, the reagent can be split/dispensed with high precision.

According to the reagent splitting/dispensing method by use of a reagent splitting nozzle having the above characteristics, when the reagent dispensing nozzle to split/dispense the reagent is in awaiting state, contamination of the operation fluid in the reagent dispensing nozzle and falling of the droplet can be prevented. Thereby, generation of the cross contamination can be prevented and the reagent can be split/dispensed with high precision.

According to the reagent splitting/dispensing mechanism having the above characteristics, the method is executed and an effect based on the method can be achieved.

DESCRIPTION OF THE PREFERRED EMBODIMENTS

Hereinafter, an embodiment of a reagent splitting/dispensing method based on a reagent dispensing nozzle and a reagent splitting/dispensing mechanism according to the present invention will be described in detail with reference to the drawings.

Figure 1:
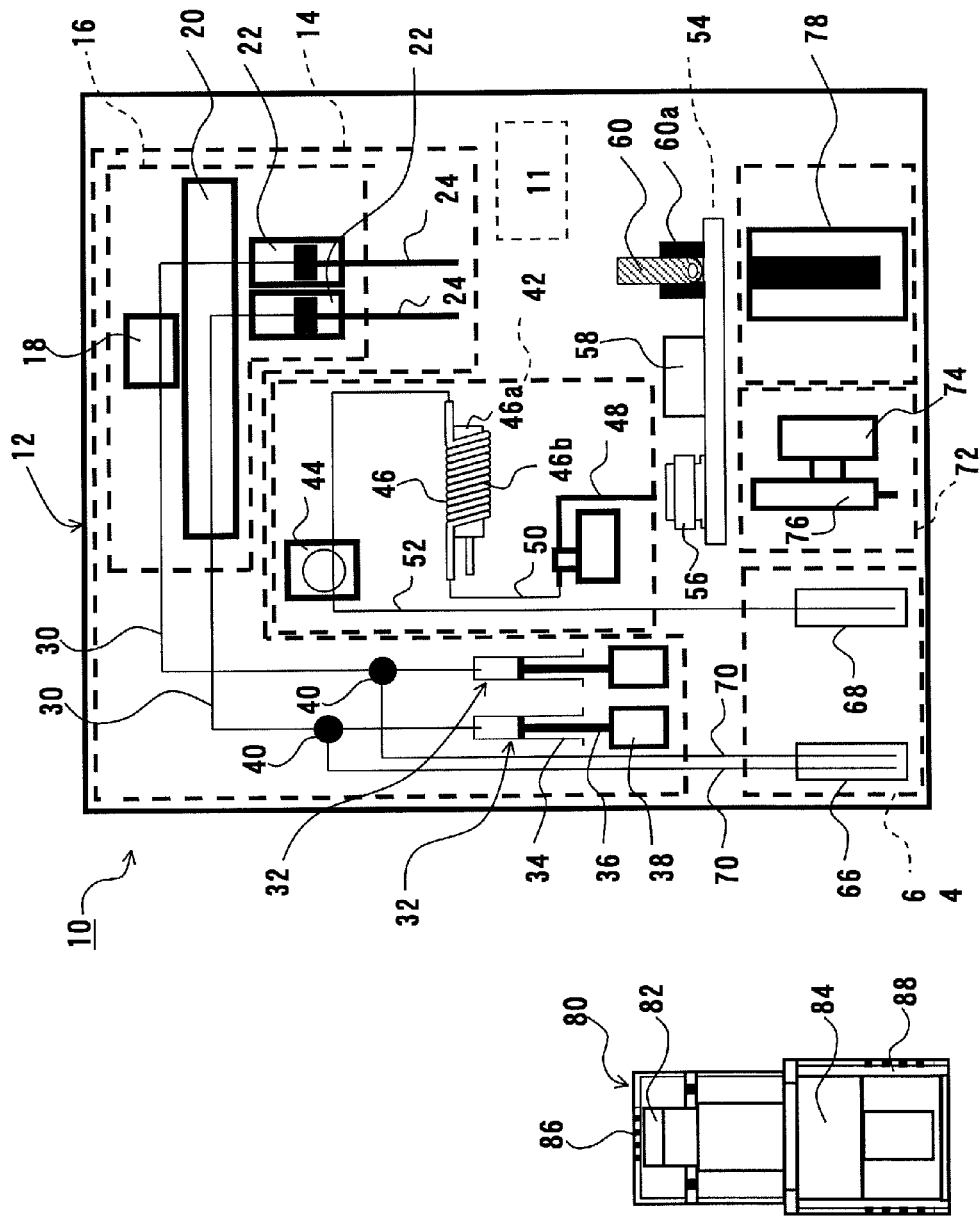
FIG. 1 is a block diagram showing the configuration of a luminescence measuring device.
Figure 2:
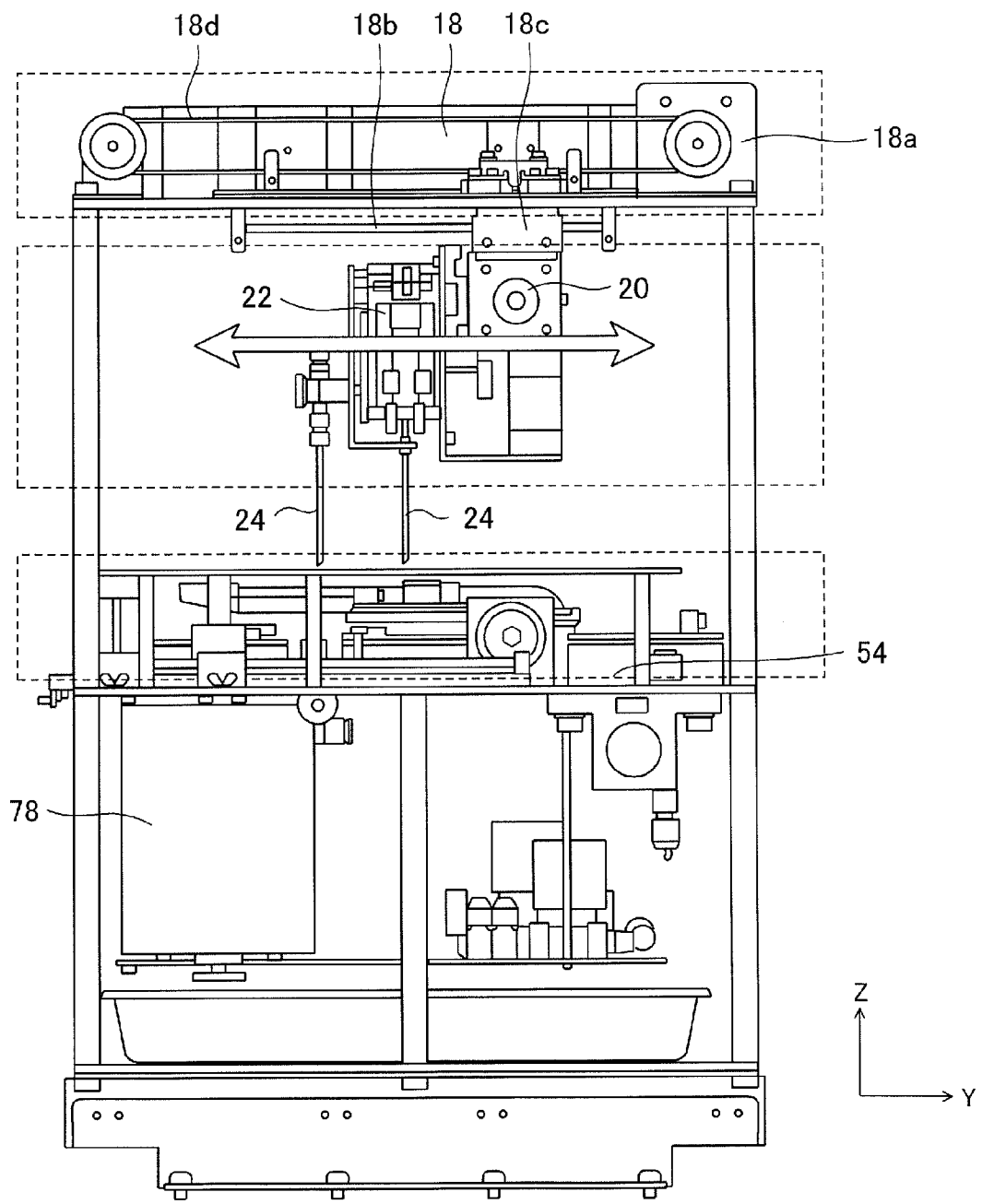
FIG. 2 is a schematic view showing the lateral configuration of a measuring unit.

First, the entire configuration of a luminescence measuring device (biomedical device) 10 that mounts a reagent splitting/dispensing mechanism according to this embodiment will be described with reference to FIG. 1. The luminescence measuring device 10 that is described in this embodiment includes a measuring unit 12 and a collecting unit 80.

The measuring unit 12 has a reagent dispensing unit 14, a hot water supply unit 42, a reagent/carrier container mounting unit 54, a buffer supply unit 64, a filter unit 72, a photomultiplier tube (PMT) unit 78, and an input/control unit (hereinafter, simply called control unit 11). These components are disposed in an outer shell.

The reagent dispensing unit 14 is configured using a triaxial actuator 16, a reagent dispensing nozzle 24, and a syringe pump (pump unit) 32 as a basic body. The triaxial actuator 16 is a unit to move the reagent dispensing nozzle to be described in detail below to the desired position. For this reason, the triaxial actuator 16 includes a Y-axis mechanism unit 18, an X-axis mechanism unit 20, and a Z-axis mechanism unit 22 to be described in detail below. The Y-axis mechanism unit 18 is disposed on a device that is rarely spatially restricted. For this reason, in the measuring unit 12 according to this embodiment, a stepping motor 18a is used as a driving actuator and a movable unit 18c that is attached to a linear guide 18b is slid by a driving belt 18d.

Meanwhile, the X-axis mechanism unit 20 and the Z-axis mechanism unit 22 attached to the movable unit 18c are difficult to have a spatial margin. For this reason, in the X-axis mechanism unit 20 and the Z-axis mechanism unit 22, a compact actuator is adopted. The compact actuator is a small actuator that is configured by incorporating a thrust axis system having a large diameter in a hollow rotor and integrating a motor and a protrusion shaft with each other. As a driving principle, a driving system is set as the stepping motor and the protrusion shaft is set as a ball screw. For this reason, positioning with high precision is realized while a size is decreased.

Figure 3A:
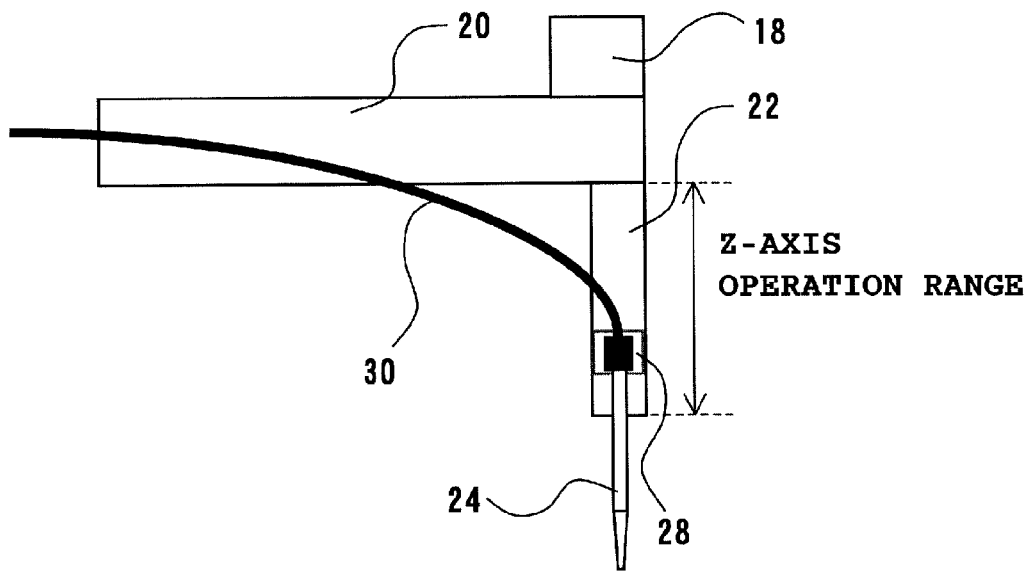
FIG. 3A is a front block diagram showing a relationship between the schematic configuration of a triaxial actuator and a reagent dispensing nozzle.
Figure 3B:
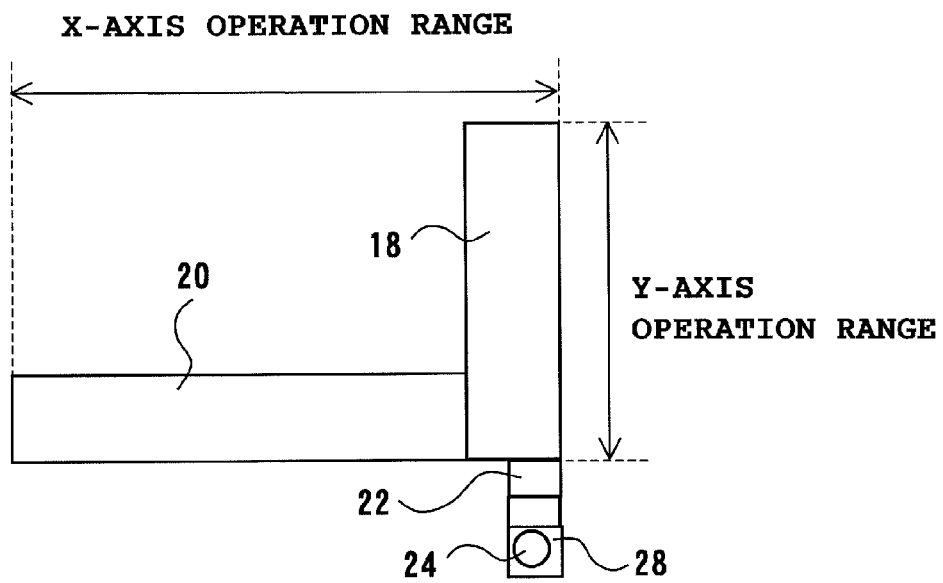
FIG. 3B is a top block diagram showing a relationship between the schematic configuration of a triaxial actuator and a reagent dispensing nozzle.
Figure 4:
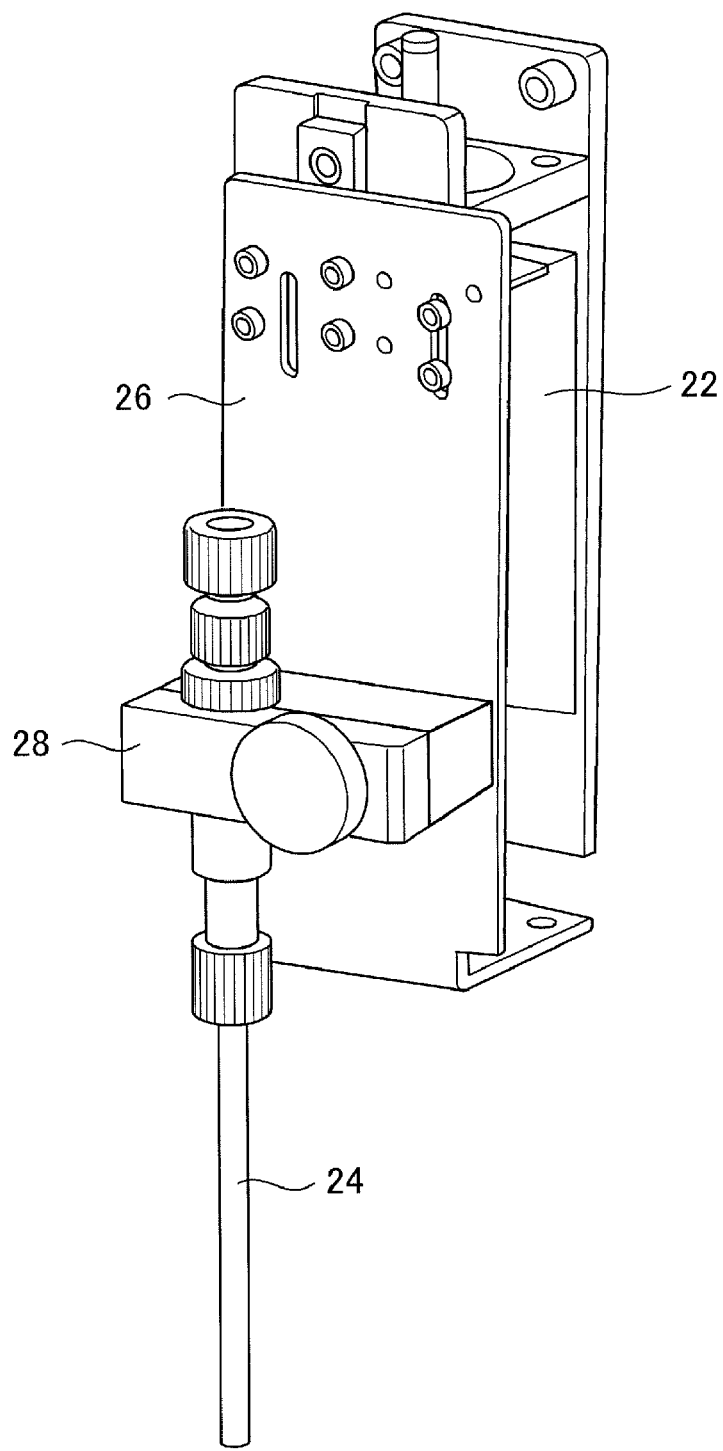
FIG. 4 is a reference perspective view showing a relationship between a Z-axis mechanism unit, a fixed block, and the reagent dispensing nozzle.

The reagent dispensing nozzle 24 is a nozzle that splits/dispenses various reagents used in luminescence measurement by the desired amount. As shown in FIGS. 3A, 3B, and 4, the reagent dispensing nozzle 24 is supported by a fixing block 28 that is included in a slide guide 26 attached to the compact actuator corresponding to the Z-axis mechanism unit 22. By adopting this support form, an elevating operation can be stabilized.

FIG. 3A is a front block diagram showing a relationship between the schematic configuration of the triaxial actuator 16 and the reagent dispensing nozzle 24. FIG. 3B is a block diagram showing the configuration of a top surface in FIG. 3A. FIG. 4 is a reference perspective view showing a relationship between the Z-axis mechanism unit 22 and the reagent dispensing nozzle 24.

To a rear end of the reagent dispensing nozzle 24, a dispensing operation tube 30 that is connected to the syringe pump 32 to be described in detail below is connected. The reagent dispensing nozzle 24 splits the reagent by applying the negative pressure to an inner part of the nozzle through the dispensing operation tube and dispenses the split reagent by applying the positive pressure to the inner part of the nozzle. The reagent dispensing nozzle 24 may be composed of a resin or metallic tube, in addition to a glass tube.

The syringe pump 32 performs a control operation of an operation fluid (pure water in this embodiment) to split/dispense the reagent by the reagent dispensing nozzle 24. The syringe pump 32 is configured using a syringe 34, a plunger 36, and an actuator 38 as a basic body. The syringe 34 is a tank that stores the pure water corresponding to the operation fluid. The plunger 36 is a pushing rod that applies the negative pressure or the positive pressure to the inner part of the syringe 34 to introduce the pure water into the syringe 34 and discharge the pure water from the syringe 34. The actuator 38 is a driving unit that pushes in or pulls out the plunger 36. If the stepping motor and the ball screw are used in the actuator 38, position control with high precision is enabled.

To a tip end of the syringe 34 in the syringe pump having the above configuration, one end of the dispensing operation tube 30 is connected. The other end of the dispensing operation tube 30 is connected to the reagent dispensing nozzle 24 described above. By connecting the dispensing operation tube 30 in the above-described way, the pure water is collected by pulling out the plunger 36 and the reagent is injected (split) into the reagent dispensing nozzle 24. In contrast, when the plunger 36 is pushed therein, the power water that is discharged from the inner part of the syringe 34 is moved to the reagent dispensing nozzle 24. For this reason, the pressure in the reagent dispensing nozzle 24 increases and the reagent that is collected in the reagent dispensing nozzle 24 is ejected (dispensed).

To the dispensing operation tube 30, the buffer supply tube 70 that is connected to the buffer supply unit 64 to be described in detail below is connected through a distribution valve 40 such as a three-way valve. By this configuration, the pure water that is the operation fluid collected in the dispensing operation tube 30 can be regularly switched. Thereby, an error of measurement data can be suppressed from being generated due to contamination of the operation fluid.

The hot water supply unit 42 supplies pure water to dilute a collection carrier. The hot water supply unit 42 is configured using a peristaltic pump 44, a heater 46, and a hot water supply nozzle 48 as a basic body. The peristaltic pump 44 is configured using a resin tube, a resin roller, and an actuator as a basic body (none of them are shown in the drawings). The resin tube is a tube that is used to send a solution and a conveyance fluid (pure water in this embodiment) flows through the resin tube. The resin tube is preferably configured to have flexibility and durability, because the resin tube may be crushed by a roller. For example, the resin tube may be composed of a silicon tube. The roller repeats the rotation and the revolution while crushing the resin tube and extrudes the conveyance fluid closed in a crushing region to a revolution direction of the roller. In the resin tube that is crushed by the roller, the power that causes a shape of the resin tube to return to an original shape works. Since the conveyance fluid is a non-compression fluid, even though plural rollers continuously revolve and extrude the conveyance fluid, the operation is continuously performed. Any actuator that can rotate the plural rollers may be used.

According to the peristaltic pump 44 having the above configuration, since a place contacting the conveyance fluid (pure water in this embodiment) is only an inner part of the tube where the conveyance fluid flows, the bump is not contaminated. For this reason, an aseptic state can be easily maintained and cleaning can be easily performed.

The heater 46 heats the pure water that is the conveyance fluid. The configuration of the heater 46 is not particularly limited. However, when the heater 46 needs to be configured to have a small size, a cartridge heater or a tube heater is preferably adopted. For example, when the cartridge heater is adopted, a metallic tube 46b may be wounded around the outer circumference of a heater body 46a and the pure water corresponding to the conveyance fluid may be circulated in the wound metallic tube 46b. This is because the pure water in the metallic tube 46b is heated by heat transmission, if the above configuration is used. When the tube heater is adopted, a rubber heater is wound around the resin tube (tube) and the conveyance fluid that is circulated in the resin tube is heated. In this configuration, if the silicon resin is used in the resin tube, a heat transfer coefficient is increased. Since the resin tube and the rubber heat are configured to have the flexibility, a degree of freedom of arrangement is high and a heated region can be secured to be long. For this reason, the temperature after heating can be avoided from being lowered, that is, the temperature can be stabilized. The arrangement position of the heater 46 is not particularly limited. However, it is preferable to decrease the solution sending distance after the heating to prevent the temperature after the heating from being lowered. Therefore, in the measuring unit 12 according to this embodiment, the heater 46 is disposed between the peristaltic pump 44 and the hot water supply nozzle 48 to be described in detail below.

The hot water supply nozzle 48 is an ejection nozzle that supplies the hot water (pure water), which is sent by the peristaltic pump 44 and heated by the heater 46, to the collection carrier cartridge 82 to be disposed in the reagent/carrier container mounting unit 54 to be described in detail below. The hot water supply nozzle may be configured using a metal (SUS) tube. Alternatively, the hot water supply nozzle 48 may be configured using a glass tube or a resin tube. To an end at the side opposite to an ejection port in the hot water supply nozzle 48, the hot water supply tube 50 that is connected to peristaltic pump 44 through the heater 46 is connected. A suction-side tube 52 in the peristaltic pump 44 is connected to the buffer supply unit 64 to be described in detail below.

According to the hot water supply unit 42 having the above configuration, the hot water can be continuously ejected from the hot water supply nozzle 48, by driving the peristaltic pump 44.

The reagent/carrier container mounting unit 54 is a stage to dispose the reagent or the collection carrier used in the luminescence measurement. In the reagent/carrier container mounting unit 54, a collection carrier cartridge holder 56, a reagent rack 58, a luminescence measuring tube holder 60a, and a water discharge port 100 are disposed. The collection carrier cartridge holder 56 is a holder to set the collection carrier cartridge 82. The collection carrier cartridge holder 56 is provided with a heat block including a heater and heats the set collection carrier cartridge 82.

Figure 5A:
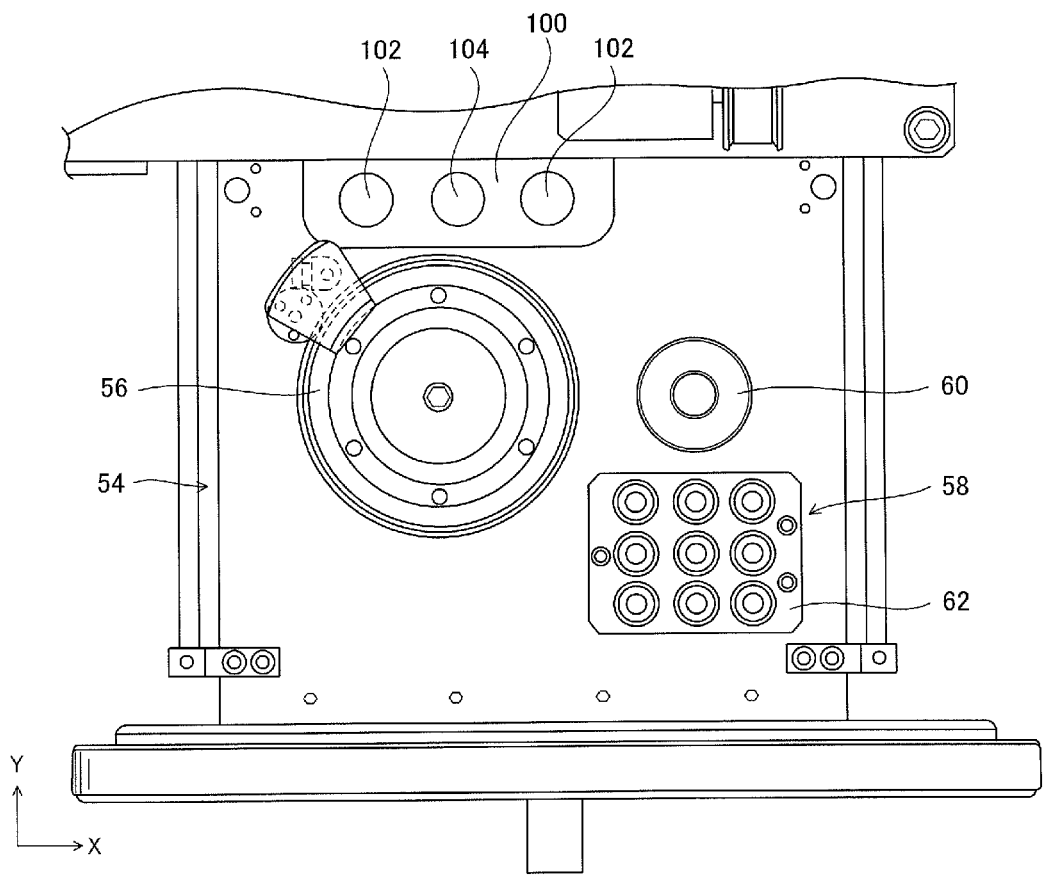
FIG. 5A is a top view showing the configuration of a reagent/carrier container mounting unit.
Figure 5B:
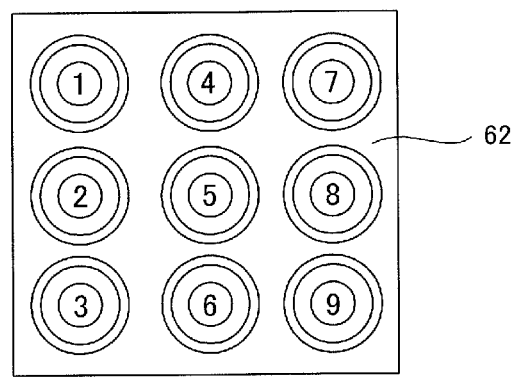
FIG. 5B is a top view showing a reagent cartridge.

In the reagent rack 58, a reagent cartridge where the reagent used in the luminescence measurement is filled is disposed. As shown in FIGS. 5A and 5B, the reagent cartridge is a package where reagents of different kinds and pure water are filled into concave parts (9 parts in an example shown in FIG. 5B) partitioned in plural parts. An upper opening of each concave part is sealed by an aluminum sheet (film). By this configuration, the reagent is not exposed to the outside, until the aluminum sheet is removed, and the reagent that is placed in stock is not contaminated by viable bacteria. FIG. 5A is a top view of the reagent/carrier container mounting unit 54 and FIG. 5B is a top view of the reagent cartridge 62.

In the luminescence measuring tube holder 60a, a luminescence measuring tube 60 is disposed. The luminescence measuring tube 60 is a micro tube that executes a luminescence reaction of the ATP extracted from the viable bacteria collected by the collection carrier cartridge 82.

The water discharge port 100 is a disposable port to discard the pure water corresponding to the operation fluid of the reagent dispensing nozzle 24 or the pure water from the hot water supply nozzle 48. The water discharge port 100 has an operation fluid discharge position 102 to discharge the operation fluid from the reagent dispensing nozzle 24 and a hot water discharge position 104 to discharge the hot water from the hot water supply nozzle 48. By regularly or periodically discharging the pure water collected in the nozzle, generation of the bacteria in the nozzle and contamination of the nozzle can be prevented. Further, an increase of the contamination in the device or generation of cross contamination can be prevented.

The buffer supply unit 64 has a reagent dispensing nozzle control water tank (hereinafter, simply referred to as control water tank 66) and a hot water supply water tank 68. In a process after the reagent dispensing nozzle 24 is used, since a process of removing isolated ATP is not included, the water (pure water) in the control water tank 66 that is filled into the dispensing operation tube 30 to link the syringe bump 32 and the reagent dispensing nozzle 24 needs to have cleanness higher than the water (pure water) in the hot water supply water tank 68. For this reason, the control water tank 66 is configured to have a small capacity and appropriately exchange the stored water, as compared with the hot water supply tank 68. Since the water in the hot water supply water tank 68 flows into the collection carrier cartridge 82 set to the collection carrier cartridge holder 56, the hot water supply water tank 68 needs to have the large capacity, as compared with the collection carrier cartridge holder 56.

The control water tank 66 that is set in the above-described way is connected to the distribution valve 40 in the dispensing operation tube 30 by the buffer supply tube 70, and the pure water can be supplied to the dispensing operation tube 30 by switching the distribution valve 40. The hot water supply water tank 68 is connected to the suction side of the peristaltic pump 44 and is sucked by driving the peristaltic pump 44.

The filter unit 72 removes the collection carrier in the collection carrier cartridge 82 that is diluted by the hot water ejected from the hot water supply nozzle 74. The filter unit 72 is configured using a suction pump 74 and a suction head 76 as a basic body. The suction pump 74 is a pump that generates the negative pressure in the suction head 76 to be described in detail below. The suction head 76 is a tubular body where a front end is opened.

In the filter unit 72 that has the above configuration, a tip end is connected to a lower part of the collection carrier cartridge holder 56, and the collection carrier that is diluted by the hot water can be sucked and removed through a collection filter 90 (refer to FIG. 6) by operating the suction pump 74.

A PMT unit 78 measures the luminescence amount of the ATP in the luminescence measuring tube 60. In the measuring unit 12 according to this embodiment, the PMT unit 78 is configured in a head-on type and is disposed on the lower part of the luminescence measuring tube 60. By this configuration, the light that is generated in the luminescence measuring tube 60 is incident from an upper part of the PMT unit 78 and the luminescence amount is measured.

The control unit 11 is an element that controls the components with respect to the input value to the luminescence measuring device and automates the luminescence measurement.

The collecting unit 80 is a device that collects the viable bacteria in the air in the collection carrier cartridge 82. The collecting unit 80 is configured using a collection carrier cartridge 82, a blast fan 84, an impactor nozzle head 86, and a discharge filter 88 as a basic body.

The collection carrier cartridge 82 collects the viable bacteria that float in the air. The collection carrier cartridge 82 includes a collection carrier 82*a* (refer to FIG. 6) to collect the viable bacteria. The collection carrier 82 that is included in the collection carrier cartridge 82 according to this embodiment forms a gel shape at the normal temperature and is solated by heating. In a lower part of the collection carrier 82*a*, a cavity (not shown) to fill diluting hot water is provided. A lower part of the cavity includes a collection filter 90 (refer to FIG. 6) that filters the hot water diluting the collection carrier 82*a*.

The blast fan 84 sucks air in the collecting unit and collides the collecting carrier 82*a* in the collection carrier cartridge 82 with the floating bacteria in the air. The blast fan 84 is preferably disposed on the downstream side (lower part side to use an upper part as a suction port in the collecting unit according to this embodiment) of the arrangement position of the collection carrier cartridge 82. In the collecting unit 80, the amount of air to be collected can be determined from the blast amount of the blast fan 84 and the operation time.

The impactor nozzle head 86 is disposed on an upper part of the collecting unit 80 and functions as a cover and an accelerator of the collection carrier cartridge 82. In order to collide the collection carrier cartridge 82 with the viable bacteria, the flow velocity of the air that flows into the collecting unit 80 needs to be fast to some degree. However, the blast fan 84 needs to be formed to have a large size or have a high rotation speed to obtain the high flow velocity, and a size of the collecting unit may be increased.

In the impactor nozzle head 86, plural ports with the small diameter are provided, and the air that is sucked by the blast fan 84 passes through the ports with the small diameter and collide the collection carrier 82*a*. When the flow volume of the air is constant, the flow velocity of the passed fluid can be increased by narrowing an area of a flow passage. For this reason, the needed flow velocity can be obtained without increasing the size or the rotation speed of the blast fan 84.

The discharge filter 88 is disposed on the downstream side (lower side in the collecting unit 80 in this embodiment) of the blast fan 84 and removes dust that is contained in the discharged air.

By this configuration, the collecting unit 80 according to this embodiment can have a small size and light weight.

Figure 6:
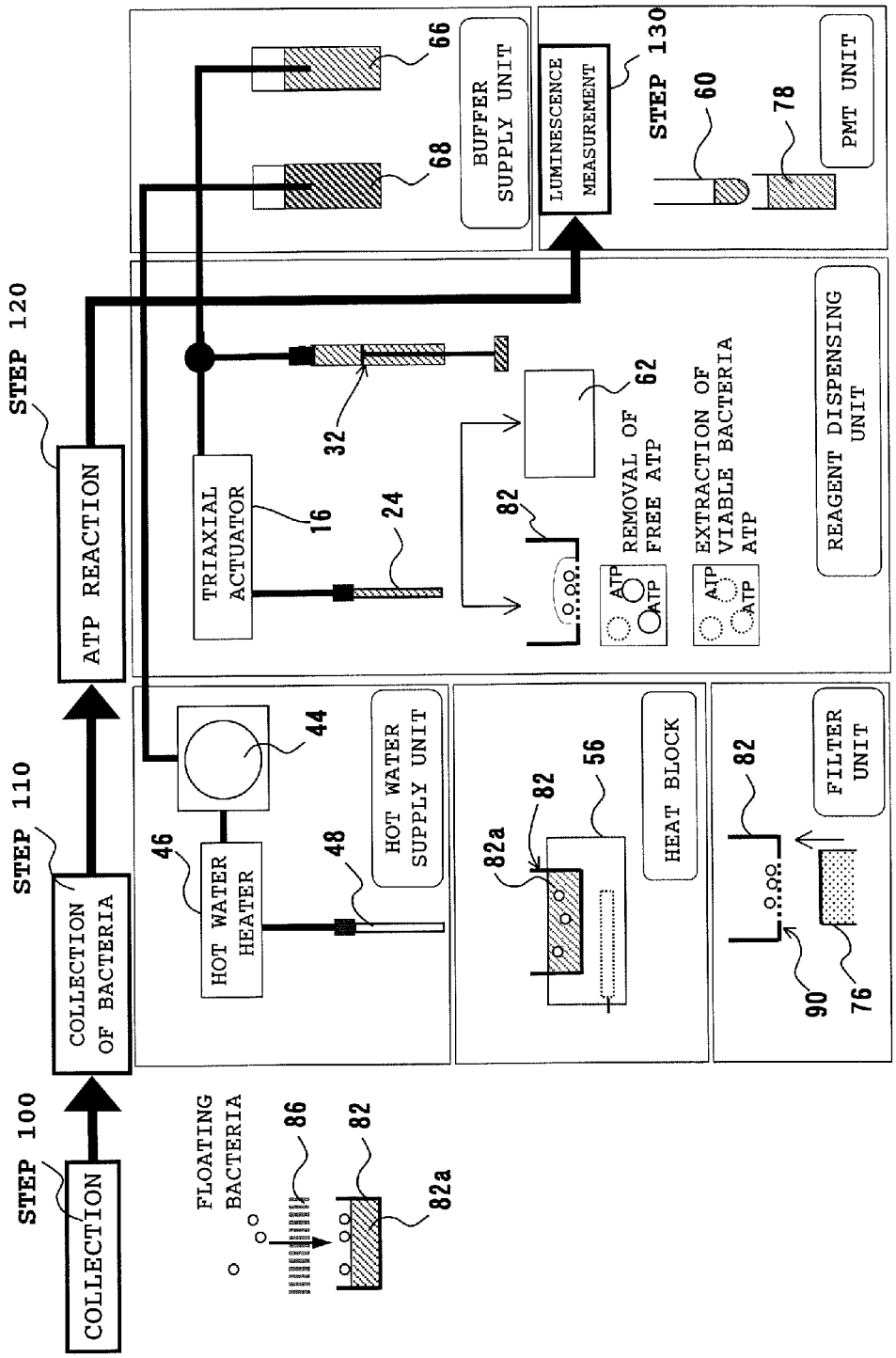
FIG. 6 is a flow view showing an aspect of luminescence measurement based on a luminescence measuring device.

In the luminescence measuring device 10 with the above configuration that includes the measuring unit 12 and the collecting unit 80, first, the viable bacteria in the air are collected by the collecting unit 80 (step 100: refer to FIG. 6).

Next, the collection carrier cartridge 82 where the viable bacteria are collected is extracted from the collecting unit 80 and the collecting unit 80 is set to the collection carrier cartridge holder 56 of the measuring unit 12. The collection carrier cartridge 82 that is set to the collection carrier cartridge holder 56 is heated by the heat block. By the heating, the collection carrier is solated. The solated collection carrier 82*a* is sucked and removed by the filter unit 72 through the collection filter 90, and the viable bacteria and the free ATP that are collected in the collection carrier 82*a* remain in the collection filter (step 110: refer to FIG. 6).

After the collection carrier 82*a* is filtered, the free ATP is removed and a viable bacteria sample is split by operating the reagent dispensing unit 14. First, the (ATP removal) reagent is split from the reagent cartridge 62 by the reagent dispensing nozzle 24, the reagent is dispensed to the collection carrier cartridge 82, and the free ATP is removed. By this work, the measurement error of the luminescence amount can be prevented from being generated due to the luminescence reaction caused by the free ATP. Next, the (ATP extraction) reagent is dispensed on the collection filter 90 in the collection carrier cartridge 82 after the free ATP is removed, and the ATP is extracted from the viable bacteria on the collection filter 90 (step 120: refer to FIG. 6).

The ATP extraction sample is split from the collection filter 90 in the collection carrier cartridge 82 and is dispensed to the luminescence measuring tube 60. In the luminescence measuring tube 60, the luminescence reagent is dispensed in advance, and the luminescence reaction starts at the same time as the dispensing of the ATP extraction sample. In the luminescence reaction in the luminescence measuring tube 60, the luminescence strength is measured by the PMP unit (step 130: refer to FIG. 6).

In the luminescence measuring device 10 that has the above configuration, the process from the splitting of the viable bacteria sample from the collection carrier cartridge 82 to the measurement of the luminescence amount is automatically executed in the measuring unit 12 that is covered with the outer shell. For this reason, the viable bacteria sample is rarely affected by the contamination. After the luminescence reagent is previously dispensed to the luminescence measuring tube 60 set to the reagent/carrier container mounting unit 54, the ATP extraction sample from the viable bacteria is dispensed. For this reason, self background light of the reagent can be measured. For this reason, a relationship between the luminescence amount and the luminescence time can be accurately obtained, and calculation of the ATP amount based on the luminescence amount, that is, measurement of the number of viable bacteria can be performed with high precision.

Figure 7:
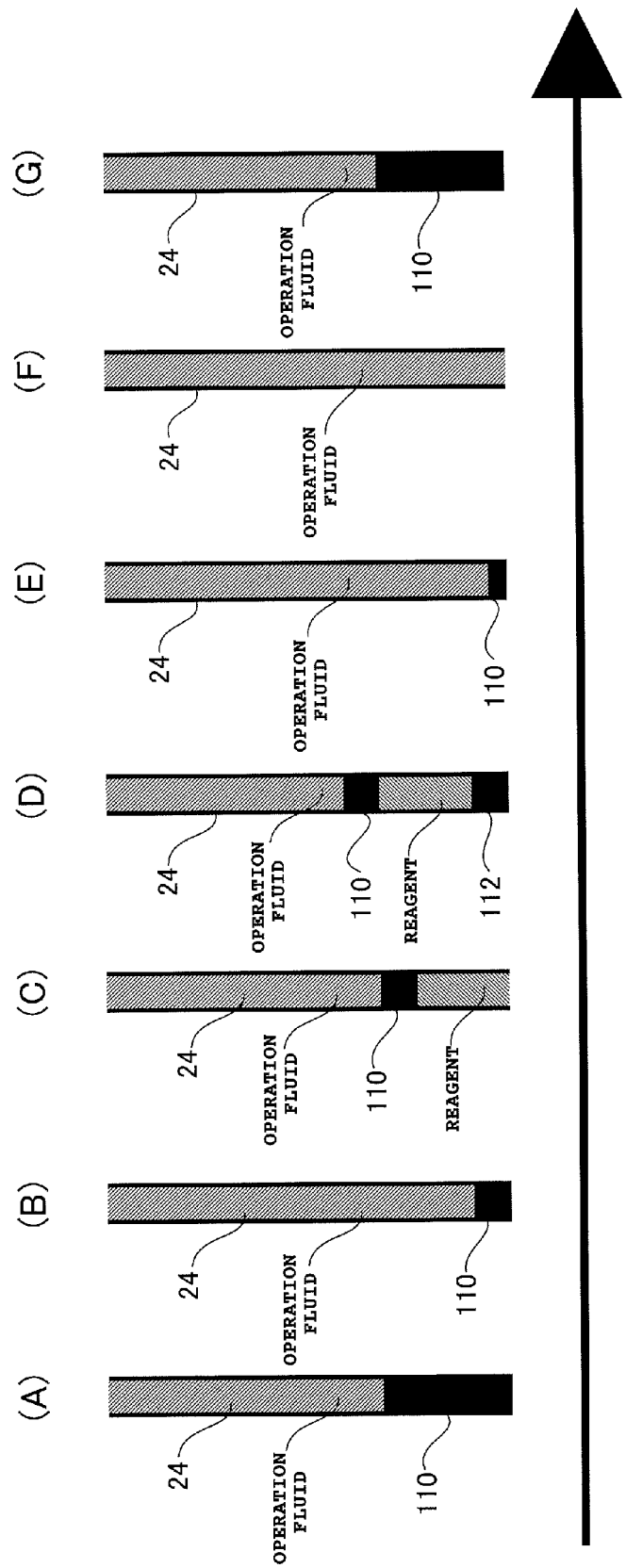
FIGS. 7A to 7G are diagrams showing a state where the reagent is split/dispensed using the reagent splitting/dispensing mechanism according to an exemplary embodiment of the invention.
Figure 8:
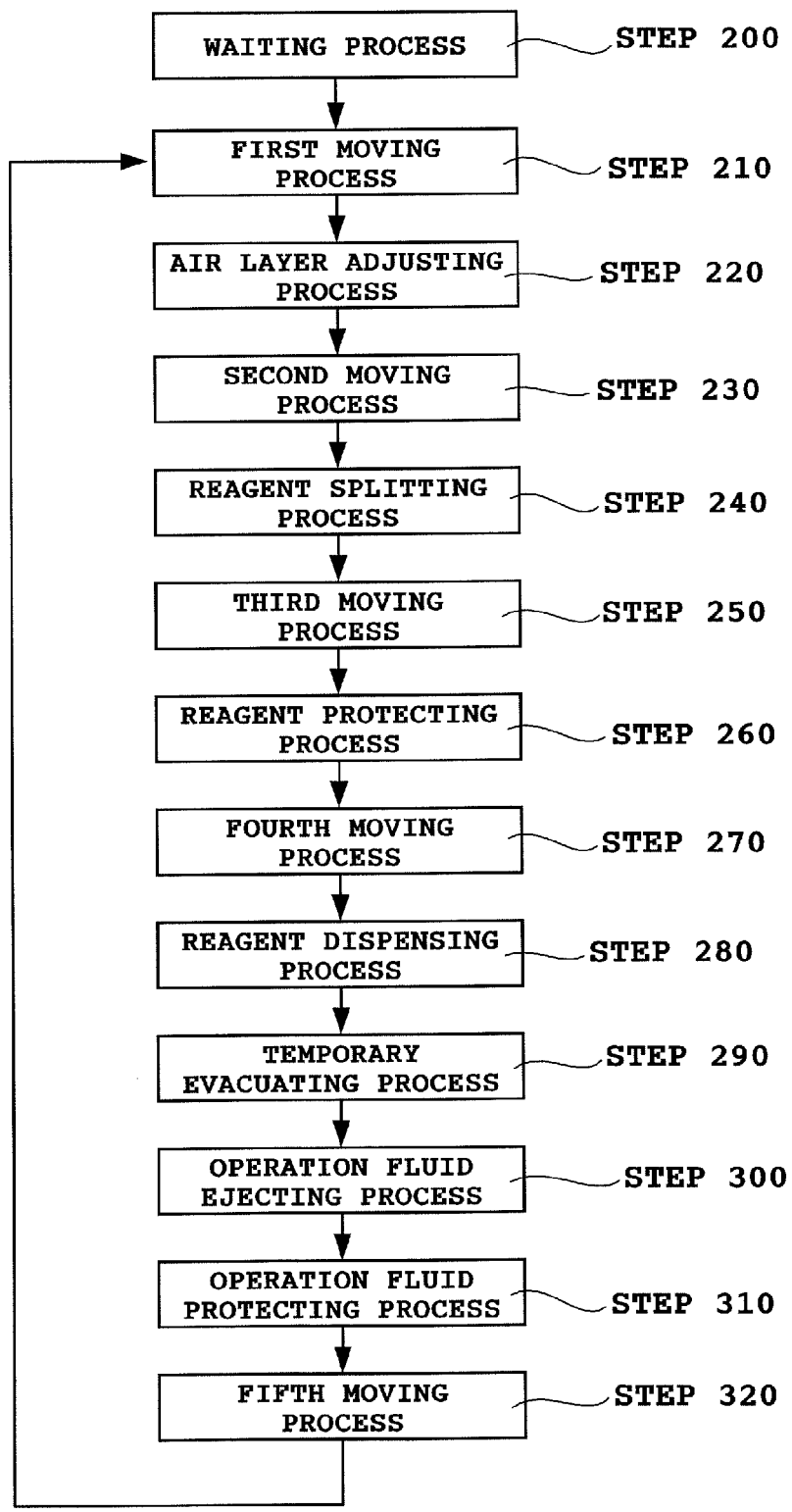
FIG. 8 is a flowchart showing each operation process in the reagent splitting/dispensing mechanism.

Next, the reagent splitting/dispensing mechanism according to this embodiment will be described with reference to FIGS. 7 and 8. FIGS. 7A to 7G are state views showing an aspect of reagent splitting/dispensing based on the reagent dispensing nozzle in the measuring unit. FIG. 8 is a flowchart showing each operation of the reagent splitting/dispensing mechanism. The reagent splitting/dispensing mechanism according to this embodiment is configured to include the reagent dispensing unit 14 and the control unit 11. In the reagent splitting/dispensing mechanism that has the above configuration, the reagent is split/dispensed as follows.

The reagent splitting/dispensing operation based on the reagent dispensing nozzle 24 is executed on the basis of a drive signal from the control unit 11 with respect to various actuators. First, in a state where the reagent dispensing nozzle 24 is at the waiting position, the control unit 11 outputs a drive signal (first air layer arrangement signal) to pull out the plunger 36 and generate the negative pressure in the syringe 34 to the actuator 38 of the syringe pump 32. The actuator 38 receives the first air layer arrangement signal and is driven. As a result, the pure water that is the operation fluid filled into the dispensing operation tube 30 and the reagent dispensing nozzle 24 flows into the syringe 34 of which the pressure becomes the negative pressure. Thereby, an occupied area of the operation fluid in the reagent dispensing nozzle 24 is decreased, and a first air layer 110 is disposed between an interface of the operation fluid and a nozzle tip end in the reagent dispensing nozzle 24. By disposing the first air layer 110 in the nozzle tip end, the operation fluid is prevented from vertically falling from the nozzle tip end in the waiting state. For this reason, generation of the cross contamination due to falling of a droplet or deterioration of splitting/dispensing precision due to the change in the reagent concentration can be prevented.

The first air layer 110 that is disposed in the waiting process preferably secures the sufficient capacity with respect to the volume of the reagent dispensing nozzle 24. In this case, the sufficient capacity may be a ratio of about 30 to 120% of the nozzle capacity. When the nozzle capacity is set as 20 μl, the capacity of the first air layer 110 may be set as 100 μL (refer to FIG. 7A: step 200: waiting process).

Next, the control unit 11 outputs a drive signal (first drive signal) to move the reagent dispensing nozzle 24 to the position right above the concave part where the reagent becoming the splitting object in the reagent cartridge 62 is filled, to the X-axis mechanism unit 20 and the Y-axis mechanism unit 18 in the triaxial actuator 16. In the waiting process described above, since the air layer (first air layer 110) having the sufficient capacity with respect to the volume of the reagent dispensing nozzle 24 is disposed in the tip end of the reagent dispensing nozzle 24, the operation fluid does not fall at the time of moving as well as waiting (step 210: first moving process).

Next, the control unit 11 outputs a drive signal (air layer adjustment signal) to push the plunger 36 and to generate the positive pressure in the syringe 34 to the actuator 38 of the syringe 32. The actuator 38 receives the air layer adjustment signal and is driven. As a result, the operation fluid is discharged from the syringe 34 of which the pressure becomes the positive pressure, and the operation fluid flows into the reagent dispensing nozzle 24 through the dispensing operation tube 30. Thereby, an occupied area of the operation fluid in the reagent dispensing nozzle 24 is increased. In this case, the air layer adjustment signal drives the actuator 38, such that a part of the first air layer 110 is discharged from the reagent dispensing nozzle 24 and the other part remains in the tip end of the reagent dispensing nozzle 24. That is, the air layer adjustment signal causes the movement amount of the plunger 36 based on the air layer adjustment signal to be smaller, as compared with the first air layer arrangement signal (refer to FIG. 7B: step 220: air layer adjusting process).

Next, the control unit 11 outputs a drive signal (second movement signal) to descend the reagent dispensing nozzle 24 and deposit the nozzle tip end in the reagent to the Z-axis mechanism unit 22 in the triaxial actuator 16 (step 230: second moving process).

Next, the control unit 11 outputs a drive signal (reagent split signal) to pull out the plunger 36 and generate the negative pressure in the syringe 34 to the actuator 38 of the syringe pump 32. The actuator 38 receives the reagent split signal and is driven. As a result, the operation fluid that is filled into the dispensing operation tube 30 and the reagent dispensing nozzle 24 flows into the syringe 34 of which the pressure becomes the negative pressure. Thereby, an occupied area of the operation fluid in the reagent dispensing nozzle 24 is decreased and the reagent that becomes the splitting object flows from the tip end of the reagent dispensing nozzle 24. By this operation, the first air layer 110 is interposed between the operation fluid and the reagent. Thereby, the operation fluid is not mixed with the reagent and generation of the cross contamination due to mixing and diffusing of the reagent or deterioration of dispensation precision of the reagent can be prevented (refer to FIG. 7C: step 240: reagent splitting process).

Next, the control unit 11 outputs a drive signal (third movement signal) to ascend the reagent dispensing nozzle 24 and evacuate the nozzle tip end from the reagent to the Z-axis mechanism unit 22 in the triaxial actuator 16 (step 250: third moving process).

Next, the control unit 11 outputs a drive signal (reagent protection signal) to pull out the plunger 36 and output generate the negative pressure in the syringe to the actuator 38 of the syringe pump 32. The actuator 38 receives the reagent protection signal and is driven. As a result, the operation fluid that is filled into the dispensing operation tube 30 and the reagent dispensing nozzle 24 flows into the syringe 34 of which the pressure becomes the negative pressure. Thereby, an occupied area of the operation fluid in the reagent dispensing nozzle 24 is decreased and the second air layer 112 is disposed between the interface of the reagent disposed in the tip end of the reagent dispensing nozzle 24 and the nozzle tip end. Thereby, dispensation precision can be prevented from being deteriorated due to vertical falling of a droplet of the reagent with respect to the nozzle tip end and the cross contamination can be prevented from being generated due to falling of the droplet (refer to FIG. 7D: step 260: reagent protecting process).

Next, the control unit 11 outputs a drive signal (fourth movement signal) to move the reagent dispensing nozzle 24 to the reagent dispensation position to the X-axis mechanism unit 20 and the Y-axis mechanism unit 18 in the triaxial actuator 16. In this case, the reagent dispensation position means an upper part of the collection carrier cartridge holder 56 or an upper part of the luminescence measuring tube 60 (step 270: fourth moving process).

Next, the control unit 11 outputs a drive signal (reagent dispensation signal) to push the plunger 36 into the actuator 38 of the syringe pump 32 and to cause the positive pressure to be generated in the syringe 34. The actuator 38 receives the reagent dispensation signal and is driven. As a result, the operation fluid is discharged from the syringe 34 of which the pressure becomes the positive pressure, and the operation fluid flows into the reagent dispensing nozzle 24 through the dispensing operation tube 30. Thereby, an occupied area of the operation fluid in the reagent dispensing nozzle 24 is increased. In this case, the reagent dispensation signal drives the actuator 38, such that the reagent filled into the reagent dispensing nozzle is ejected and a part of the first air layer 110 remains in the tip end of the reagent dispensing nozzle. By this operation, the split reagent can be completely dispensed and the operation fluid can be prevented from being ejected (refer to FIG. 7E: step 280: reagent dispensing process).

Next, the control unit 11 outputs a drive signal (temporary evacuation signal) to move the reagent dispensing nozzle 24 to the operation fluid discharge position 102 in the water discharge port 100 to the X-axis mechanism unit 20 and the Y-axis mechanism unit 18 in the triaxial actuator 16 (step 290: temporary evacuating process).

Next, the control unit 11 outputs a drive signal (operation fluid ejection signal) to push the plunger 36 into the actuator 38 of the syringe 32 and to cause the positive pressure to be generated in the syringe 34. The actuator 38 receives the operation fluid ejection signal and is driven. As a result, the operation fluid is discharged from the syringe 34 of which the pressure becomes the positive pressure, and the operation fluid flows into the reagent dispensing nozzle 24 through the dispensing operation tube 30. The amount of flowing operation fluid exceeds the allowed amount of the nozzle and a part of the operation fluid is ejected to the operation fluid discharge position 102. The operation fluid of the ejected amount is replenished from the control water tank 66 by controlling the distribution valve 40 disposed in the dispensing operation tube 30 and operating the actuator 38 to pull out the plunger 36 (refer to FIG. 7F: step 300: operation fluid ejecting process).

Next, the control unit 11 outputs a drive signal (operation fluid protection signal) to pull out the plunger 36 and generate the negative pressure in the syringe 34 to the actuator 38 of the syringe pump 32. The actuator 38 receives the operation fluid protection signal and is driven. As a result, the operation fluid that is filled into the dispensing operation tube 30 and the reagent dispensing nozzle 24 flows into the syringe of which the pressure becomes the negative pressure. Thereby, an occupied area of the operation fluid in the reagent dispensing nozzle 24 is decreased and the first air layer 110 is disposed between the interface of the operation fluid filled into the reagent dispensing nozzle 24 and the nozzle tip end. In this case, the disposed first air layer 110 is set to have the same capacity as that of the first air layer 110 disposed in the waiting process described above (refer to FIG. 7G: step 310: operation fluid protecting process).

Next, the control unit 11 outputs a drive signal (fifth movement signal) to move the reagent dispensing nozzle 24 to the waiting position to the X-axis mechanism unit 20 and the Y-axis mechanism unit 18 in the triaxial actuator 16 (step 320: fifth moving process).

When the reagent is dispensed again after the fifth moving process ends, the repetitive control from the first moving process (step 210) is executed.

According to the reagent splitting/dispensing mechanism where the above control is performed under the above configuration, when the reagent dispensing nozzle 24 to split/dispense the reagent is in the waiting state, the operation fluid in the reagent dispensing nozzle 24 can be suppressed from being contaminated. The droplet can be prevented from falling at the time of the movement operation, and the cross contamination can be prevented from being generated. Thereby, the reagent splitting/dispensing operation can be performed with high precision.

What is claimed is:

1. A reagent splitting/dispensing method based on a reagent dispensing nozzle that controls a split amount or a dispensation amount of a reagent by an operation fluid disposed in the reagent dispensing nozzle, the reagent splitting/dispensing method comprising:
    a waiting process of disposing a first air layer between an interface of the operation fluid and a nozzle tip end in the reagent dispensing nozzle;
    a first moving process of moving the reagent dispensing nozzle to a position above the reagent to be split;
    a second moving process of depositing the nozzle tip end in the reagent;
    an air layer adjusting process of increasing the occupation amount of the operation fluid in the reagent dispensing nozzle and decreasing the occupation amount of the first air layer, between the first moving process and the second moving process;
    a reagent splitting process of decreasing the occupation amount of the operation fluid in the reagent dispensing nozzle and filling the reagent into the reagent dispensing nozzle from the nozzle tip end;
    a third moving process of evacuating the tip end of the reagent dispensing nozzle from the reagent;
    a reagent protecting process of disposing a second air layer between an interface of the split reagent and the nozzle tip end;
    a fourth moving process of moving the reagent dispensing nozzle to a reagent dispensation position, after the reagent protecting process;
    a reagent dispensing process of increasing the occupation amount of the operation fluid in the reagent dispensing nozzle and ejecting the split reagent;
    an operation fluid protecting process of disposing the first air layer between the interface of the operation fluid and the nozzle tip end, after dispensing the reagent; and
    a fifth moving process of evacuating the reagent dispensing nozzle to a waiting position, in a state where the first air layer is disposed between the interface of the operation fluid and the nozzle tip end.

2. The reagent splitting/dispensing method according to claim 1, further comprising:
    a temporary evacuating process of moving the reagent dispensing nozzle to an operation fluid discharge position after the reagent dispensing process; and
    an operation fluid ejecting process of ejecting a part of the operation fluid from the nozzle tip end, at the operation fluid discharge position.

3. The reagent splitting/dispensing method according to claim 2,
    wherein, in the reagent dispensing process, the process proceeds to the temporary evacuating process, after the first air layer remains.

4. A reagent splitting/dispensing mechanism comprising:
    a triaxial actuator in which a movement axis in a horizontal direction is set to an X axis and a Y axis and a movement axis in a vertical direction is set to a Z axis;
    a reagent dispensing nozzle which is moved by the triaxial actuator;
    a pump unit which is connected to the reagent dispensing nozzle and controls an operation fluid disposed in the reagent dispensing nozzle; and
    a control unit which outputs a first air layer arrangement signal to decrease the occupation amount of the operation fluid in the nozzle and dispose a first air layer between an interface of the operation fluid and a nozzle tip end in the reagent dispensing nozzle to the pump unit, outputs a first movement signal to move the reagent dispensing nozzle to the position above the reagent to be split and a second movement signal to deposit the nozzle tip end in the reagent to the triaxial actuator after the first air layer is disposed in the reagent dispensing nozzle, outputs an air layer adjustment signal to increase the occupation amount of the operation fluid in the reagent dispensing nozzle to the pump unit, between the output of the first movement signal and the output of the second movement signal, outputs a reagent split signal to decrease the occupation amount of the operation fluid in the nozzle and fill the reagent into the reagent dispensing nozzle from the nozzle tip end to the pump unit after the nozzle tip end is deposited in the reagent, outputs a third movement signal to evacuate the tip end of the reagent dispensing nozzle from the reagent to the triaxial actuator, outputs a reagent protection signal to dispose a second air layer between an interface of the split reagent and the nozzle tip end to the pump unit, outputs a fourth movement signal to move the reagent dispensing nozzle to a reagent dispensation position to the triaxial actuator, after the second air layer is disposed in the reagent dispensing nozzle, outputs a reagent dispensation signal to increase the occupation amount of the operation fluid in the reagent dispensing nozzle and eject the reagent to the pump unit, after the reagent dispensing nozzle reaches the reagent dispensation position, outputs an operation fluid protection signal to decrease the occupation amount of the operation fluid in the reagent dispensing nozzle and dispose the first air layer between the interface of the operation fluid and the nozzle tip end to the pump unit, after the reagent is elected from the reagent dispensing nozzle, and outputs a fifth movement signal to evacuate the reagent dispensing nozzle where the first air layer is disposed after the reagent is dispensed to a waiting position to the triaxial actuator.

5. The reagent splitting/dispensing mechanism according to claim 4,
wherein the control unit outputs a temporary evacuation signal to move the reagent dispensing nozzle to an operation fluid discharge position to the triaxial actuator, after the reagent dispensation signal is output, and the control unit outputs an operation fluid ejection signal to increase the occupation amount of the operation fluid in the reagent dispensing nozzle to eject a part of the operation fluid from the tip end of the reagent dispensing nozzle moved to the operation fluid discharge position, to the pump unit.

6. The reagent splitting/dispensing mechanism according to claim 4,
wherein the reagent dispensation signal is a signal to control the occupation amount of the operation fluid to completely eject the reagent filled into the reagent dispensing nozzle and eject a part of the first air layer.

7. The reagent splitting/dispensing mechanism according to claim 4,
wherein the pump unit is a syringe pump.

* * * * *